United States Patent [19]

Day et al.

[11] 4,109,243

[45] Aug. 22, 1978

[54] DATA SEQUENCE DISPLAY SYSTEM AND TIME-COMPRESSION SYSTEM THEREFOR

[75] Inventors: Christopher Cameron Day, Newtonville; Robert Lee Cannon, Waltham, both of Mass.

[73] Assignee: American Optical Corporation, Southbridge, Mass.

[21] Appl. No.: 680,017

[22] Filed: Apr. 26, 1976

[51] Int. Cl.² ............................................. G06K 15/18
[52] U.S. Cl. .......................... 340/324 R; 179/15.55 T; 346/33 ME; 346/110 R
[58] Field of Search ............. 340/324 R; 346/33 ME, 346/110 R; 235/92 EA, 92 DE, 92 CV, 92 NG, 92 SH; 360/7, 8, 9; 179/1 SP, 15.55 T

[56] References Cited

U.S. PATENT DOCUMENTS

| | | | |
|---|---|---|---|
| 2,676,206 | 4/1954 | Bennett et al. | 179/1 SP |
| 3,585,440 | 6/1971 | Lee et al. | 340/324 AD |
| 3,763,328 | 10/1973 | Lester et al. | 179/15.55 T |
| 3,789,137 | 1/1974 | Newell | 179/15.55 T |
| 3,855,424 | 12/1974 | Tharmaratnam et al. | 360/9 X |
| 3,916,323 | 10/1975 | Moriyama et al. | 235/92 SH |
| 3,951,135 | 4/1976 | Goldberg et al. | 346/33 ME |

*Primary Examiner*—David L. Trafton

*Attorney, Agent, or Firm*—Jeremiah J. Duggan; Stephen A. Schneeberger

[57] ABSTRACT

A system for the cyclical time-compression of a signal waveform, particularly applicable to displays. Continuous input data is temporarily stored, as in a recirculating memory, during the trace and retrace phases (B & A) of a processing or display operation. The stored data is subsequently read out in time-compressed form during the trace phase (B) of the cycle. The average rate at which data is read out of storage is faster than the average rate at which it is entered, the ratio of average readout rate to average entry rate being the compression ratio of the system and corresponding herein with the ratio of a full display sweep cycle to the trace portion of that cycle such that the initial waveform, time-compressed, is displayed in its entirety. In an illustrated embodiment, the data is entered into a recirculating memory at a rate resulting in apparent precession of the data in memory. When the memory is "full", data is read out at a rate, here syncopated, which on average is faster than the rate at which it enters. In this embodiment, the time-compression ratio is essentially $n+1/n$, where $n$ is an integer representative of the length of the trace phase of a trace-retrace display cycle. The data samples read out of memory at a syncopated rate are retimed to avoid distortion in the output waveform.

14 Claims, 6 Drawing Figures

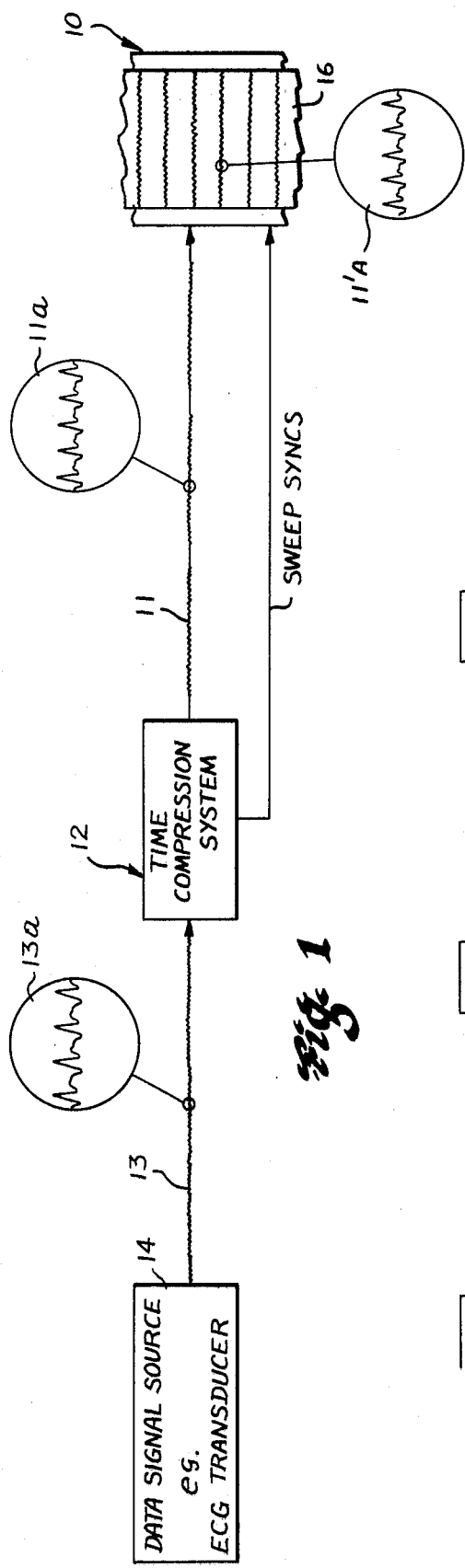
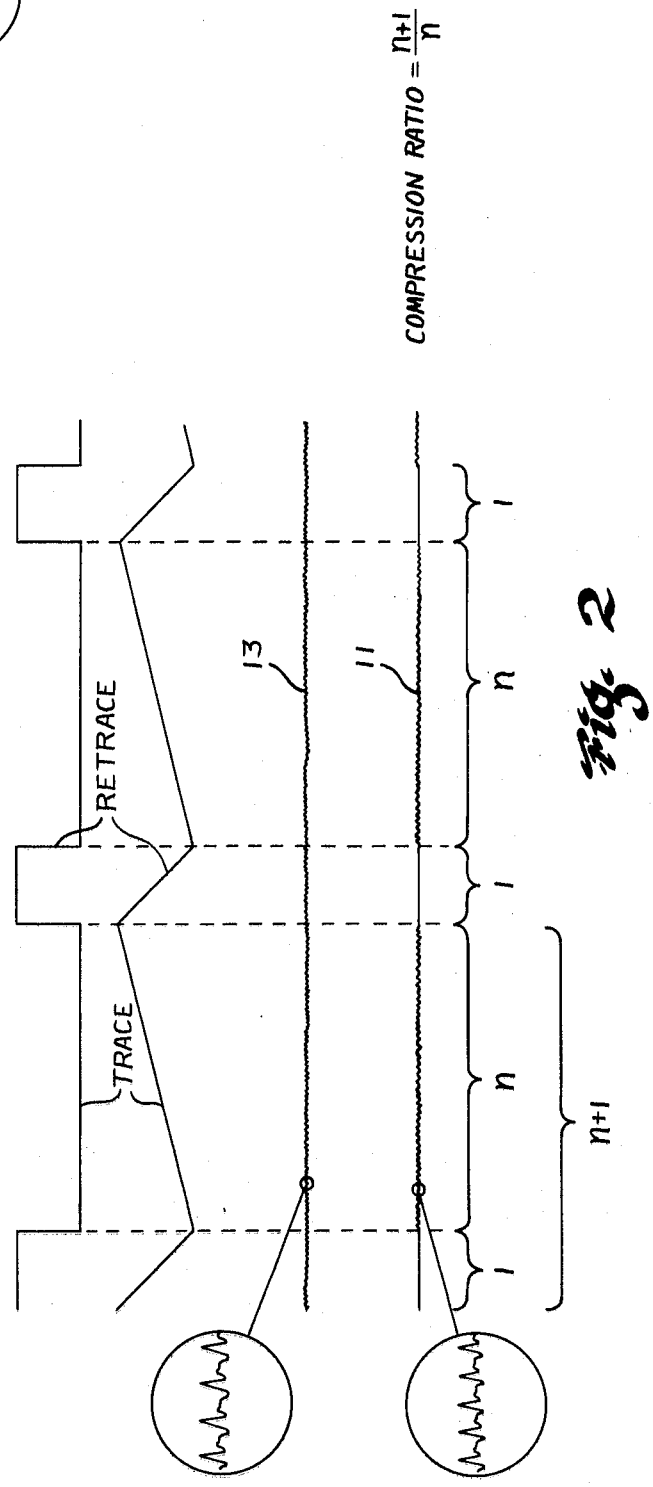
Fig. 1
Fig. 2

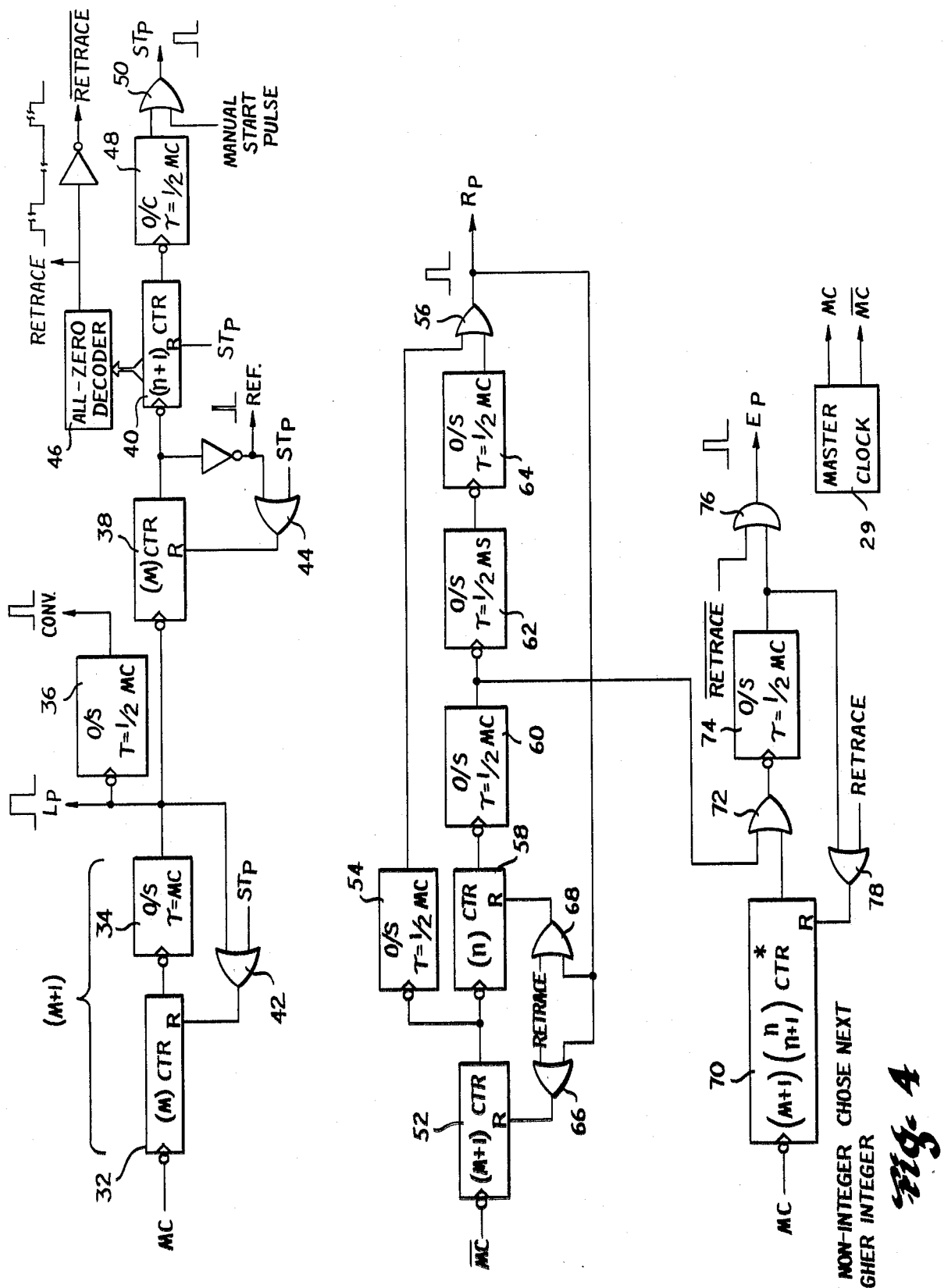

DATA SEQUENCE DISPLAY SYSTEM AND TIME-COMPRESSION SYSTEM THEREFOR

This invention relates to data processing systems, and more particularly to signal waveform display systems. More specifically still, the invention relates to signal waveform time-compression systems.

While the invention relates to data processing systems generally, it is particularly applicable to the display of physiological waveform data from patients, as in electrocardiography and the like. Typically such waveforms have been recorded by means of continuous-trace strip chart recorders which, while providing a record of excellent quality, generate large amounts of paper which do not lend themselves to incorporation into the patient's records.

A flat-page chart or wide strip chart with the waveform written in a raster-type format may be more convenient from the standpoint of record storage and waveform comparison. Recorders capable of permanently recording the waveform in a raster type format such as is used with cathode ray tubes, are known. When using such raster format display media, the information or waveform to be displayed is normally continuous and comprises a continuous input to the chart recorder. The information applied to the input of the display device during the "trace" phase of each trace-retrace cycle of the raster format is written or traced out, however, the information appearing at the input during the "retrace" phase of the display cycle is "blanked", or not written, and is normally lost.

Even in certain display systems which do not utilize a trace/retrace type raster, as for instance the helical scan recorder described in U.S. Pat. No. 3,893,453 entitled COMPRESSED DATA DISPLAY SYSTEM issued on July 8, 1975 in the name of Goldberg et al and assigned to American Optical Corporation, the assignee of the present invention, it may be desirable to periodically interrupt the waveform input signals to the display to create a blank zone or margin for the entry or display of other data. As used hereinafter, the term "retrace", is intended to apply similarly to the "blank" phase or margin in equipment of the type in the immediately aforementioned example.

While in some instances the loss of information occurring during the retrace or signal blanking period may be tolerable, this is not normally so in display systems for waveforms containing physiological information of a patient. In these latter display systems as well as others, it is desirable to retain and display all of the information received from the data source. The retrace portion of a display raster may comprise as much as 10% or more of each trace-retrace cycle and thus, the amount of information which may be lost during "retrace" may be significant.

If a display system utilizing a trace/retrace or trace/blank cyclical format is to be employed and all of the continuously available waveform data is to be displayed, the waveform processing system must be capable of storing data during the retrace or blank phase of each display cycle. If the system is operating in real time and data is stored during each retrace period for subsequent write out during a trace period, there remains the problem that new data must also be written out during the trace period. If that new data is itself stored until the previously stored data is routinely read out, it is evident that there will be an increasing, and ultimately excessive, amount of data for storage in successive cycles. Even if the system is not operating in real time, continuous input to the waveform processing system is desired due to the complexities of otherwise stopping and starting a tape or similar off-line storage device for the retrace portion of each display cycle.

Accordingly, it is an object of the invention to provide a new and improved data sequence processing system. More specifically, it is an object of the invention to provide a new and improved signal waveform processing system of the type having a trace/retrace or similar multi-phased operation which displays substantially all of a substantially continuous input waveform during only the trace phase (or similar portion) of the operation.

It is a still further object of the invention to provide a new and improved signal waveform processing system of the type described which is of relatively simple, inexpensive and/or efficient design.

In accordance with the principles of the invention, there is provided a system for the time-compression of a continuous data sequence, as from a waveform, which continuously receives and temporarily stores waveform data during the trace and retrace phases (phases B & A) of a processing or display operation or cycle and which subsequently reads out substantially all of the stored data in a time-compressed form during the trace phase (phase B) of the cycle. The average rate at which data is read out of storage is faster than the average rate at which it is entered into storage, the ratio of the average readout rate to the average entry rate being the compression ratio of the system and corresponding herein with the ratio of a full display sweep cycle to the trace portion of that cycle. The resulting data which is read out from the time-compression system may be applied to the input of display means and comprises the initial signal waveform now in time-compressed form, such that the initial waveform is displayed in its entirety.

The waveform data is sampled, as by conversion from an analog form to a digital form, and the sampled data is entered in a memory at a predetermined rate. The storage capacity of the memory and rate of data entry into memory are selected such that the memory is filled during the retrace phase of each display cycle. Following completion of the retrace phase and during the trace phase of the display cycle, and while new data continues to be entered into memory, data previously in memory is read out at a rate, or rates, such that the total storage delay of the memory is shortened or decremented from a maximum to a minimum over the trace phase of the cycle thereby presenting in a time-compressed format all, or at least a representative portion of the data occurring during the cycle.

Hypothetically, if one were provided with a "hose-pipe" type memory having fixed data input and output "locations" and it were possible to periodically shorten or decrement the delay-time length of the memory by "physically deleting" delay increments from the intermediate portion of the memory, one might realize the desired time-compression. However, because of the impracticality or impossibility of actually realizing a memory of such physical configuration, the requisite time-compression is provided with a memory of fixed physical size through an apparent deletion of delay increments by appropriate timing of data input and data read out.

In a particular embodiment of the invention, the memory is a fixed-access recirculating type of predetermined time-quantized length and data is entered in memory at a rate such that the data appears to precess or advance in memory relative to each successive transfer of data thereinto. The memory is repetitively interrogated and data read out at two different intervals, one interval corresponding with the interval between successive entries of data words into memory and the other interval being substantially less such that the total number of data words read out of memory during the trace phase of a display cycle is the same, or substantially the same, as the number of data words occurring and entered into memory during both the trace and retrace phases of the cycle. The two different intervals at which the memory is interrogated are interleaved, or interspersed, resulting in a syncopated rhythm of data read out from memory.

This digital data from the memory is then reclocked at a substantially constant rate preparatory to reconversion to analog form in order that the subsequently displayed waveform may appear as an undistorted, time-compressed replica of the original signal waveform presented to the time-compression system.

The interspersing of the different intervals at which the memory is interrogated comprises, in an illustrative embodiment, successively interrogating the memory $n$ times at the same interval as for data entry into memory, and following by the shorter interval with a single interrogation. The quantity $n$ is a number representative of the ratio of the length of the trace portion of a display sweep cycle to the length of the retrace portion thereof and in the illustrative embodiment is an integer.

Further objects, features and advantages of the invention will become apparent upon consideration of the following detailed description in conjunction with the drawing, in which:

FIG. 1 is a functional block diagram of a waveform display system incorporating the time-compression system of the invention;

FIG. 2 depicts several waveforms which will be helpful in understanding the concept and operation of the time-compression system;

FIG. 4 is a generalized schematic representation of the control timing generator of the illustrative time-compression system;

Figures 3, 6:
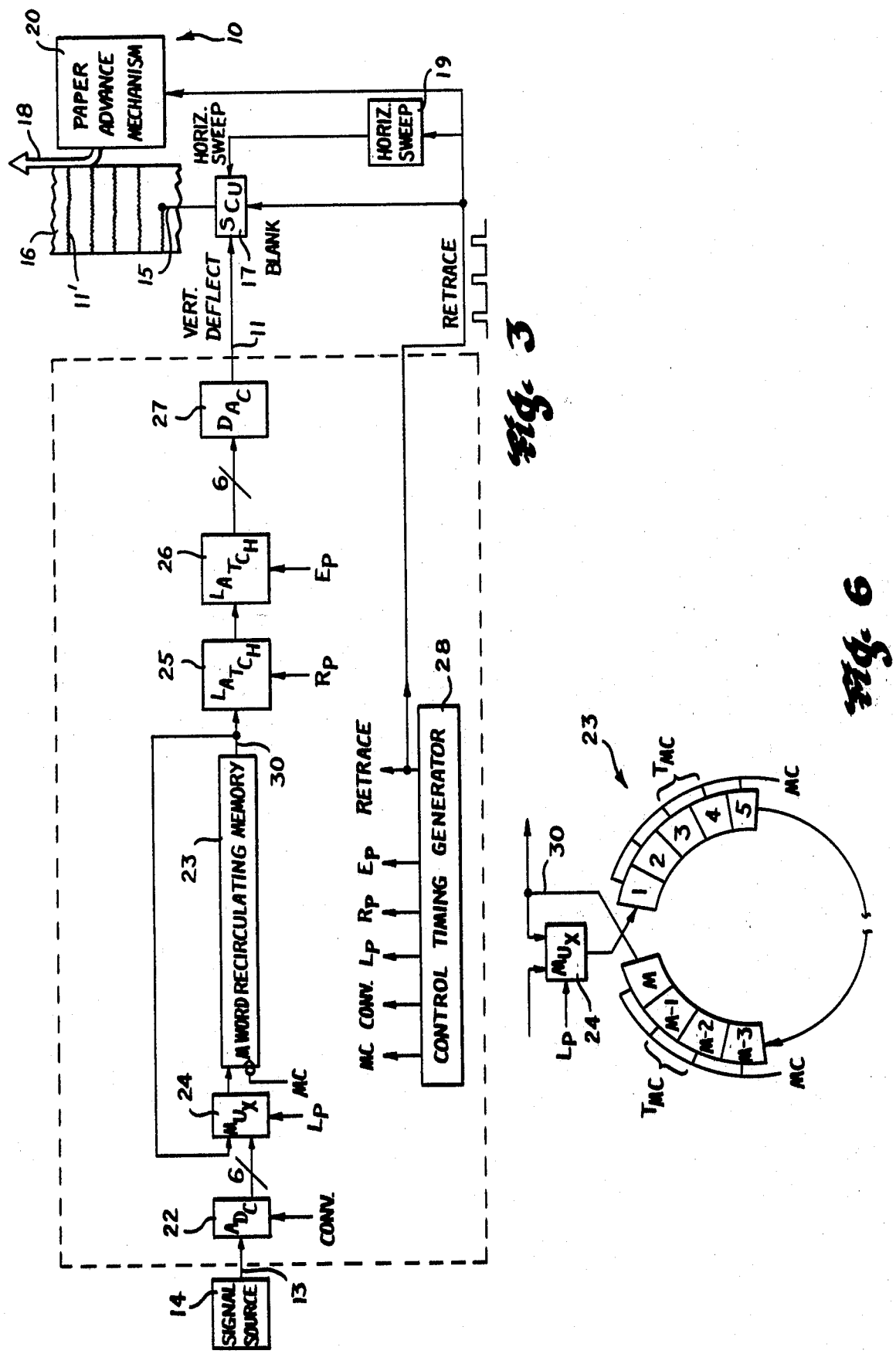
FIG. 3 is a more detailed block diagram of the display system of FIG. 1 showing the time-compression system of the illustrative embodiment of the invention in greater detail.
FIG. 6 depicts, in enlarged, functionalized form, the recirculating memory of the illustrative time-compression system of FIG. 2.

The system of FIG. 1 includes a cyclically operating display device, such as the strip chart recorder 10, for receiving and displaying a signal waveform (11, 11') in time-compressed form from novel time-compression system 12 which receives a real-time based signal waveform 13 from a data signal source 14. The real-time based signal waveform 13 in the illustrative embodiment is a continuous analog ECG waveform and correspondingly, signal source 14 may be an ECG transducer, a playback recorder or the like. Alternatively, waveform 13 may be some other waveform, either physiological or non-physiological, requiring display of substantially its full informational content.

The illustrated display recorder 10, seen in greater detail in FIG. 3, is of a type in which a stylus 15 permanently records input information on a strip chart 16 adapted to move in incremental steps relative to recorder 10 and stylus 15 in the direction indicated by arrow 18. Stylus control unit 17 operates in a known manner to cyclically move stylus 15 transversely (horizontally in FIGS. 1 & 3) of the direction of movement of strip chart 16 to provide the horizontal trace and retrace phases of a conventional raster format display cycle.

Horizontal movement of stylus 15 is controlled by horizontal sweep circuit 19 controlled by the RETRACE control signal from time-compression system 12. The RETRACE control signal appears as the uppermost waveform in FIG. 2 and synchronizes the operation of sweep circuit 19. Horizontal sweep circuit 19 applies a control signal such as the sawtooth waveform of FIG. 2, to the stylus control unit 17, the direction and slope of that control signal being indicative of the direction and speed with which control unit 17 moves the stylus 15 across strip chart 16. This sawtooth waveform and its function are the same as that of the horizontal sweep sawtooth in a cathode-ray tube display. It will be appreciated that the control signal from sweep circuit 19 might assume a different form, such as the RETRACE signal itself, if the stylus control unit 17 includes a 2-speed bidirectional motor for horizontal movement of the stylus. Further still, the sweep for recorder 10 might be generated independently of time-compression system 12, as with a synchronous motor for the helical scan recorder of the aforementioned U.S. Pat. No. 3,893,453, in which case a sync signal originating at the recorder might be extended to the time-compression system to synchronize it with the recorder each sweep cycle.

Following each trace sweep of stylus 15 and during the retrace sweep phase, strip chart 16 is stepped by the chart advance mechanism 20 which is actuated by each positive transition of the RETRACE control signal. It will be appreciated, however, that a chart advancing mechanism providing continuous advance of strip chart 16 might alternatively be provided, in which case the time-compressed written waveform 11' appearing on strip chart 16 has a slight downward slope to the right.

The relative timing of the trace and retrace phases of the horizontal sweep of stylus 15 is controlled by the RETRACE control signal from time-compression system 12 in which the trace phase is "$n$" times as long as the retrace phase, where "$n$" is an integer. In the illustrative embodiment, the ratio of the trace phase to the retrace phase of each horizontal sweep cycle (i.e. $n$) is selected as a binary-based integer in order to facilitate the generation of the various timing signals to be hereinafter described. Accordingly, the length of the full cycle may be represented as $n + 1$, where $n$ is the length of the trace phase. The time-compression ratio to be hereinafter discussed comprises $n+1/n$, where $n+1$ represents the length of a full cycle and $n$ represents the length of the trace phase thereof. In a typical system, the retrace phase of the sweep cycle might by ⅛ or 1/10 of the length of the trace phase; however, the retrace phase in the illustrated embodiment is selected to be ¼ the length of the trace phase to facilitate illustration and explanation of the inventive concept. Accordingly, in FIG. 2 and throughout this discussion, the expression $n$ assumes a value of 4 and the so-called compression ratio is 5/4. If chart paper 16 is assumed to be relatively wide and the speed of the horizontal trace to be relatively slow, the trace phase of a horizontal sweep cycle may be 40 seconds, with the retrace being 10 seconds.

During the retrace phase of each horizontal sweep, a blanking signal provided by the RETRACE control signal from time-compression system 12 is applied to the stylus 15 through control unit 17. During the blanked horizontal retrace of stylus 15 (illustrated by dotted lines on strip chart 16), time-compression system 12 is operative to store incoming data from source 14, that stored data and the data occurring during the subsequent trace phase of the horizontal sweep being presented as time-compressed analog waveform 11 (11' on strip chart 16). It will be appreciated that recorder 10 might alternatively take the form of the helical scan recorder of the aforementioned U.S. Pat. No. 3,893,453, in which case the "retrace" phase of a display cycle might be replaced with a phase which either blanks the display or admits data to the vertical deflection input of control unit 17 from a source other than time-compression system 12 and source 14.

Through reference to the expanded portion 13a of waveform 13 and the expanded portion 11a of waveform 11 in FIGS. 1 & 2, both portions being of identical length in actual time, it will be seen that the characteristic PQRST complex of a heartbeat appears four times in portion 13a, whereas five such complexes appear in portion 11a. The 5:4 time compression of waveform 13 by the time-compression system 12 permits all the data occurring in a 50-second interval to be compressed and presented to the recorder 10 as a vertical deflection signal during the 40-seconds required for the trace phase of the horizontal sweep. Similarily, the remaining 10 seconds of each actual 50 second output from compression system 12 occupy the retrace phase of the horizontal display sweep and contain no data. In this manner, all of the data in waveform 13 is displayed and/or recorded in a time-compressed form on recorder 12, with no loss of data during the retrace phase of each horizontal sweep. A description of the time-compression system 12 of the invention is contained hereinbelow.

Referring generally to the time-compression system 12 depicted in FIG. 3, analog data from signal source 14 is periodically converted to a multi-bit digital signal by an analog/digital converter 22 and the resulting digital data stream is selectively entered and temporarily stored in a recirculating memory 23 through multiplexer 24. Digital data is selectively read out of recirculating memory 23 by a first data latch 25, is retimed through a second data latch 26 and is reconverted to analog form by digital/analog converter 27 for controlling the vertical deflection of recorder stylus 15. Timing of the various data processing operations in time-compression system 12 is controlled by the control timing generator 28. The 5:4 compression of data is accomplished by continuously entering data words into memory 23 during the entire horizontal sweep cycle (10 second retrace; 40 second trace) and reading the data out of memory during the trace phase of the display cycle at an average rate which is 5/4th the rate at which data is entered into the memory.

The A/D converter 22 converts the waveform from signal source 14 to a multi-bit digital signal or word which appears in parallel on six output lines (vis, a 6-bit digitally coded signal, a binary code being suitable). Conversion of the analog waveform to the digitally coded signal is timed by a CONVERT (CONV) signal provided by control timing generator 28. General reference may be made to FIGS. 4 & 5 for an understanding of the generation and relative timing of the various timing and control signals discussed herein. The repetition rate of the CONV signals is much greater than the repetition rate of the ECG signal, for example, one-hundred times greater. Thus, ECG signals occurring in real-time might have a repetition rate of about one per second and the CONV signal might suitably have a repetition rate of one-hundred per second. The sampling rate permits a sufficient number of digital samples of the waveform to be taken for digital processing and subsequent reconversion to an analog form containing substantially all of the initial information. It will be noted that whereas A/D converter 22 provides digital signals on 6 output lines, only one of these lines is illustrated in FIG. 3. The remaining five digital data processing channels between A/D converter 22 and D-A converter 27 are identical to that depicted in FIG. 3. More specifically, multiplexer 24, memory 23 and latches 25 and 26 each have the capability of processing six-bit parallel data words, though not specifically illustrated.

The illustrated recirculating memory 23 is of a type having limited access and may comprise a dynamic shift register having a serial length of M words, where M represents the product of the number of digital samplings of the analog waveform by A/D converter 22 occurring in one second and the time-quantized length of the retrace phase of the horizontal sweep cycle. The time quantized length of memory 23 is the product of the number of shift registers (M) and the period of the register shift clock, $^TMC$. In the illustrated embodiment, the waveform 13 is converted to digital data samples about one-hundred times a second and the retrace period is about 10 seconds and thus, memory 23 has a storage capacity of one-thousand 6-bit parallel digital data words. It will be appreciated that the M word recirculating memory might be represented as a shift register containing M 6-bit parallel storage stages as illustrated in FIG. 6. By using a serially accessed, synchronously clocked shift register type of memory, relatively inexpensive, standardized integrated circuitry may be employed.

The master clock 29 (seen in FIG. 4) generates two square waveforms MC and $\overline{MC}$ which are the inverse of one another. The clock squarewwave (or pulses) MC conveniently occur at a rate of one-hundred kHz, the period between successive MC pulses being $^TMC$. Because of the length of the memory 23 shift register (one-thousand storage stages), synchronous shifting of data from one stage to the next is accomplished by applying MC shift pulses to each stage of the shift register, as seen in FIG. 6. The storage and logic elements employed throughout time-compression system 12 are assumed for the purposes of illustration to be edge-triggered by the zero-going or negative-going edge of a respective timing pulse applied thereto.

Data words in memory 23 are shifted from left to right by MC pulses as illustrated in FIG. 3 (clockwise as illustrated in FIG. 6). During recirculation, each word appearing at the final stage "M" of memory 23 is returned to the first state "1" through a switch or multiplexer 24. Alternatively, a new word from A/D converter 22 is entered into stage "1" of recirculating memory 23 through multiplexer 24 when a load pulse $^LP$ is applied to the multiplexer. Digital multiplexer 24, as earlier noted, has two groups of six-inputs; one six-input group for the six output lines of A/D converter 22 and the other six-input group for reentering data for recirculation from the six outputs of the final stage of the memory shift register.

The data recirculating in memory 23 appears to precess with each successive entry of a new data word into memory. This precession is accomplished in the illustrated embodiment by strobing the multiplexer with a load pulse $^LP$ to enter a new data word in memory each time M + 1 shifts of data in memory 23 have occurred and permits a new word to take the place of the oldest word stored in the memory. In this way, current data is entered into memory 23 replacing the oldest data. This operation for continuously entering new data into memory at periodic intervals is similar to that described in U.S. Pat. No. 3,768,093 for Digital CRT System for Displaying a Precessing Waveform and its Derivative issued Oct. 23, 1973 to C. C. Day and assigned to the assignee herein; however, it will be noted that the apparent precession of data in-memory relative to the data-entering strobe in the aforementioned patent is in a direction contra to the normal serial data shift direction, whereas in the embodiment illustrated herein the apparent precession of data is in the same direction as the serial data shift. This difference arises because of a strobe interval somewhat less than the time-quantized length of the memory in the instance of the patent and a strobe interval somewhat greater than the time-quantized length of the memory 23 in the present instance. It is necessary in the illustrated embodiment that the precession of data in memory 23 be in the forward direction in order that the storage delay length of the memory may be decremented in the manner to be hereinafter explained.

Figure 5:
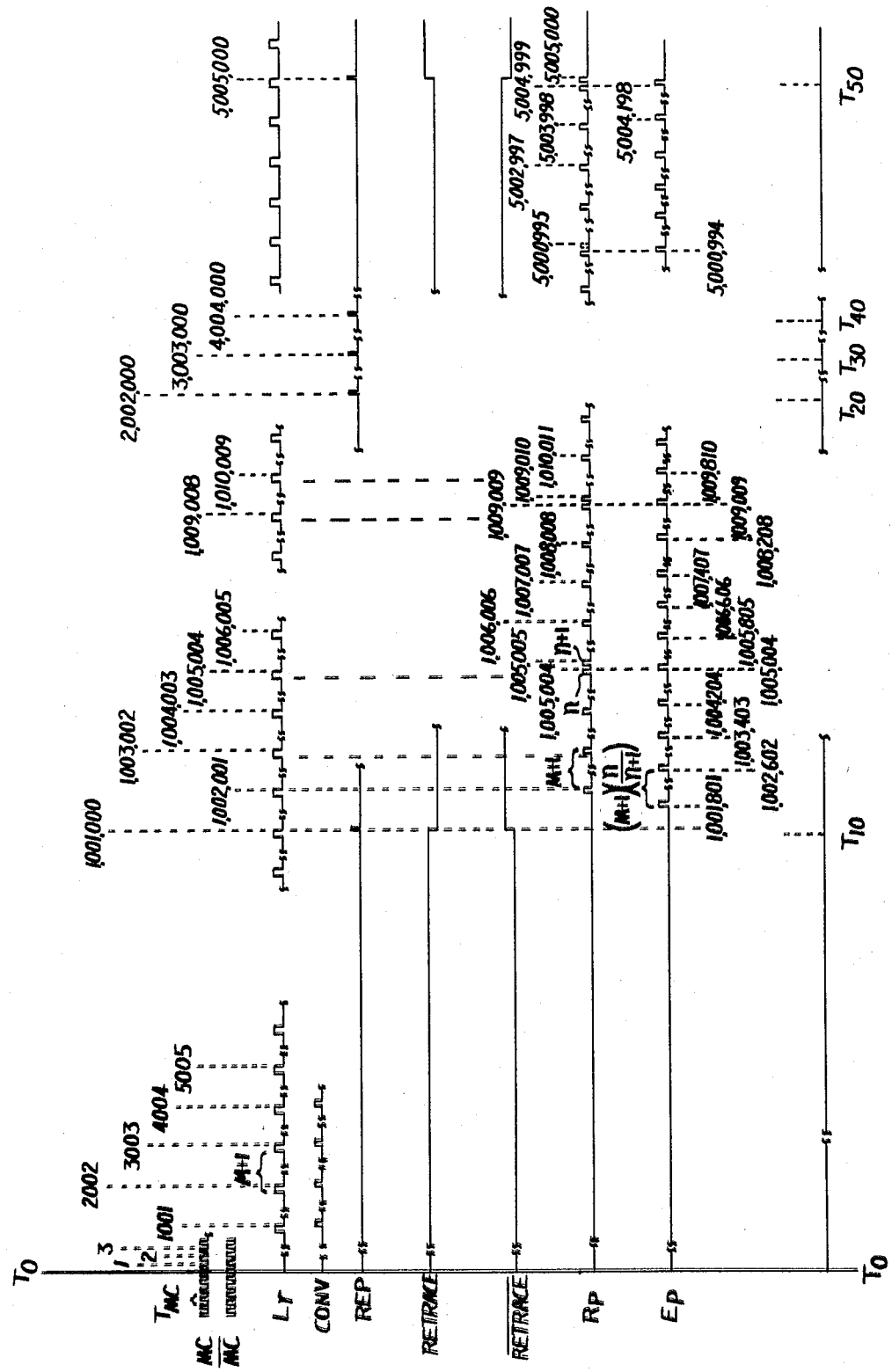
FIG. 5 depicts various timing waveforms from the timing generator of FIG. 4 which will be helpful in understanding the operation of the illustrative embodiment of the invention.

It will be appreciated that the A/D conversion signals CONV and the data entry strobes $^LP$ recur at the same rate (about 100 times per second) but in time-shifted relation to each other to permit development of the digital sample prior to its entry into memory 23, as will be evident in the description of the timing diagram of FIG. 5.

Assuming for all intents and purposes that the memory 23 is "empty" at the beginning of the retrace phase of a sweep cycle, one thousand successive data entry pulses $^LP$ result in the entry of one thousand successive digital data words in the memory, thereby "filling" the memory. The memory-filling operation is timed to coincide with the length of the retrace phase of the sweep cycle, following which memory 23 is selectively interrogated to read out the stored data.

The data word temporarily stored in the "last" or Mth (1000th) stage of memory register 23 is extended not only to an input of multiplexer 24 by conductor 30, but also to the input of 6-bit latch 25. The latch 25 is strobed by a train of read pulses, $^RP$ occurring at an average rate which is 5/4 the rate of the data entry pulses, $^LP$. This ratio of the rate of read pulse $^RP$ to that of entry pulses $^LP$ comprise the compression ratio, $n+1/n$. More specifically, in the illustrated embodiment read pulses $^RP$ recur at two different interspersed intervals, with four (i.e. $n$) successive $^RP$ pulses occurring at the same interval ([M + 1] times $^TMC$) as the data entry pulses $^LP$ and a fifth (i.e. $n+1$th) $^RP$ pulse following the fourth pulse by the period of successive clock pulses $^TMC$. In this recursive sequence, four data words are read out of memory 23 at the same rate at which they entered and continue to enter, and the read out of the fifth word upon the next following clock cycle results in the next similar five-word sequence being resynchronized to the starting point established by the fifth word of the preceeding sequence such that each successive sequence is time-shifted by one period of the master clock, $^TMC$.

Stated another way, by including the additional $^RP$ pulse occurring at the short interval following each four pulses recurring at the longer interval, the total storage delay of the memory 23 is shortened or decremented by the product of ($^TMC$) and (M), which represents the time-quantized length of the memory for one pass therethrough. Further, because the data was loaded into memory 23 in a manner resulting in the apparent forward precession of data relative to the $^LP$ pulses, the data is correctly ordered for this sequence of $^RP$ pulses. Each successive sequence of five $^RP$ pulses operates to decrement the total storage delay by the time-quantized length of memory 23. Repetition of this five $^RP$ pulse sequence M-1 times (i.e. 999 times) operates to decrement the total storage delay of a word circulating in memory 23 from a maximum (1000 times the time-quantized length of the memory) to a minimum (the singular time-quantized length of the memory). As mentioned, the time-quantized length of the memory 23 refers to the product of master clock period $^TMC$ and the number of shift register stages in a single pass of data through memory 23, and the total storage delay experienced by a word in memory 23 is determined by the product of the time-quantized length of memory 23 and the number of passes therethrough.

Each successive data word is entered in memory 23 at the interval of the respective entry control pulses $^LP$ (i.e. [M + 1] [$^TMC$]) and the first four $^RP$ pulses in the trace phase recur at the same interval (as $^LP$) such that the full storage delay length of the memory from stage 1 to stage M is used before each of the respective four data words is read out to latch 25; however, the rapidly following fifth $^RP$ pulse creates the appearance that the M-1th stage of the shift register is being read out, even though it occurs at the Mth stage, having the effect of advancing the read out of that associated data word by the time-quantized length of memory 23 and shifting the reference from which the next four data bytes appear to occur from the Mth stage to the M-1th stage.

The next four $^RP$ pulses (pulses 6–9) recurring at the longer intervals are now referenced to the fifth pulse such that it continues to appear that stage M-1 is being read out. It will be remembered that the "normal", or longer, interval between pulses (i.e. [M + 1] [$^TMC$]) provide one stage of precession of a data word with each successive circuit through the memory 23. The tenth $^RP$ pulse follows the ninth pulse by the same short interval ($^TMC$) as the fifth pulse with the similar result that it then appears that stage M-2 is being read out and the total storage delay experienced by a respective data word has decreased again by the time-quantized length of memory 23. The read out of $n + 1$ words for each $n$ word being stored during the trace phase of the sweep by cyclically decrementing the total storage delay of the memory results in all of the data entered in memory 23 during the full horizontal sweep cycle being read out in the trace phase thereof.

The output of 6-bit data latch 25 is extended to the input of the 6-bit data latch 26. Latch 26 is strobed by a train of timing equalization pulses, $^EP$, to load the respective data words appearing at the input thereto. The $^EP$ pulses occur during the trace phase of each sweep cycle at a constant repetition rate which serves to retime or reclock the data read out of memory 23 by the $^RP$ pulses. This retiming of the data output from the memory 23 and latch 25 is desirable to avoid the distortion which would otherwise appear in the time-compressed waveform displayed following conversion of the digital data stream to analog signal 11 by D/A converter 27.

The $^EP$ pulses have a repetition rate such that each of the data words read out of memory 23 by $^RP$ pulses during the trace portion of a sweep cycle is retimed by a respective $^EP$ pulse. Stated another way, for $(n + 1)$ words $(M)(5 \times 1000 = 5,000)$ stored during a full sweep cycle, $(n + 1)$ (M) [e.g. 5000] $^EP$ pulses are provided during the trace phase of the cycle. The $^EP$ pulses recur at an interval which is substantially $(^TMC)$ $(M+1)$ $(n/n+1)$. Care is taken, as will be seen in the discussion of the control timing circuitry of FIG. 4, to insure that an $^EP$ pulse occurs appropriately in the brief interval between the nth and the $n+1$th $^RP$ pulses of each recursive sequence of $n+1$ pulses in the $^RP$ pulse train, thereby assuring that each data word loaded into latch 25 is subsequently loaded into latch 26 and contributes to the reformulated analog waveform 11.

The output of latch 26 is extended to the input of 6-bit D/A converter 27 which converts the digital data stream to the electrical time-compressed analog 11 which is traced out on recorder 10 as waveform 11'. Electrical analog waveform signal 11 is extended to an input of stylus control unit for controlling the vertical deflection of stylus 15 during each horizontal sweep cycle.

Referring now to FIGS. 4 & 5 in greater detail, an explanation of the circuitry of control timing generator 28 and the relative timing of signals follows. The CONV, $^LP$ $^RP$, $^EP$ and RETRACE timing pulses or control signals are provided by various counters and associated circuitry which may conveniently be provided by circuitry available in the TTL, CMOS, ECL logic families and/or the like. It should be understood, however, that the general concept of the invention is capable of generally similar implementation using appropriate analog circuits and memory. While the output of each converter might simply be illustrated as a pulse, FIG. 4, instead includes representative one-shot circuits for developing the various pulses. Reference should be made to the timing diagram of FIG. 5 for the relative (and actual) timing of the various control signals. Because of the difficulty in showing all events of significance during a sweep cycle on a constant, or even logarithmic, time scale, certain liberty has been taken in changing time scales in FIG. 5 and reference should be made to the included numbers which represent elapse of the indicated number of master clock cycles.

The MC squarewave from master clock 29 is extended to the input of counter 32 which provides a negative-going transition at the output of counter 32 following M (1000) successive cycles (negative transitions) of MC. The output of (M) counter 32 is extended to a one-shot 34, having a period corresponding to $^TMC$. The timing of one-shot 34 as well as the other one-shots to be hereinafter discussed, may be controlled by clocking means synchronous with the master clock or by R-C time constants. The data entry pulse $^LP$ appears at the output of one-shot 34 for extension to multiplexer 24 and additionally to the input of one-shot 36. One-shot 36 has a period corresponding to ½ MC and its output comprises convert pulse, CONV, at the end of the $^LP$ pulse. The first CONV pulse occurs after the first $^LP$ pulse and thus, data may not be converted from A/D form for entry into memory by the first $^LP$ pulse; however, the digital sample resulting from the first CONV pulse is available for entry when the next $^LP$ pulse occurs nearly one full cycle later. The loss of the first digital sample is inconsequential.

It should be noted that (M) counter 32 and one-shot 34 combine to establish an interval of M + 1 clock pulses between successive $^LP$ (and also CONV) pulses, thereby enabling the precessive entry of data into memory 23. The output of one-shot 34 is fed back to the reset input of counter 32 through OR gate 42 in order to reset the counter during the $^LP$ pulse.

The output of one-shot 34 is also extended to the input of an (M) counter 38 which, in essence, counts the number of digital samples entered into memory 23. Each time M data words are entered, the counter 38 undergoes a 1-to-0 transition at its output, that output transition being extended to the input of $(n + 1)$ counter 40 for controlling the count therein. The inverted output of (M) counter 38 is fed back to the reset input of counter 38 through OR gate 44, resulting in the brief pulse, Ref, which is shown only for the purpose of illustrating the output from counter 38.

The stages of the $(n + 1)$ counter 40 remain in an "all zero" state until, the first output from counter 38, at which time at least one stage of counter 40 goes to a "one" state. In as much as the first output from counter 38 is concurrent with the Mth (1000th) $^LP$ pulse and signifies "fill-up" of memory 23 with M data bytes, this event signals transition from the retrace phase to the trace phase of the sweep cycle. An "all zero" decoder 46 accepts outputs from the several stages of $(n + 1)$ counter 40 and provides a RETRACE signal (logic "1" state) at its output while all stages of counter 40 are in the zero state. Similarly, a $\overline{RETRACE}$ signal is provided which is in the logic "1" state when the RETRACE signal is in the logic "0" state. A negative-going transition appears at the output of counter 40 upon the $n + 1$th (5th) output from counter 38 and acts, through one-shot 48 having a period of ½ MC and OR gate 50, to provide a start pulse, $^{ST}P$. Alternatively, a manually generated start pulse may be extended to an input of OR gate 50 to provide the $^{ST}P$ pulse therefrom. The $^{ST}P$ pulse is extended to the reset inputs of counters 32 and 38 through OR gates 42 and 44 respectively, and directly to the reset input of counter 40 for initialization of the counters at the start of each retrace/trace sweep cycle.

Referring to the generation of the $^RP$ pulse, the inverted phase of the master clock, $\overline{MC}$, is applied to the input of (M+1) counter 52 to provide a negative-going transition at its output upon each count of M + 1 clock pulses $\overline{MC}$. The output of counter 52 is extended to the input of a one-shot 54 having a period of ½ MC for producing the $^RP$ pulse which is extended to one input of OR gate 56. The output of counter 52 is also extended to the input of (n) counter 58 to provide a negative-transition at the output of counter 58 when each nth $^RP$ pulse following reset occurs.

Counter 58, and three one-shots 60, 62, & 64 connected in series to the output of the counter, serve to generate a $n+1$th $^RP$ pulse following each reset, the $n+1$th $^RP$ pulse following the nth $^RP$ pulse by an interval of $^TMC$. Each one-shot 60, 62, & 64 has a period of ½ MC and the $^RP$ pulse is thus also of ½ MC duration. The output of one-shot 64 is extended to another input of OR gate 56 which provides the $^RP$ pulse at its output.

The $^RP$ pulses are extended through OR gates 66 & 68 to the reset inputs of counters 52 & 58 respectively for resetting the counters at each instance of the $^RP$ pulse. The reset initiated by the $n+1$th $^RP$ pulse effectively resynchronizes the next sequence of $n+1$ $^RP$ pulses to a new starting point shifted one $^TMC$ from the previous sequence. Both counters 52 & 58 are prevented from counting and providing $^RP$ pulses during the retrace phase of a sweep cycle by extending the RETRACE signal to their respective reset inputs through OR gates 66 & 68 respectively.

The time-plot of $^RP$ pulses in FIG. 5 illustrates the time relationship of data readout from memory 23 relative to data entry represented by the $^LP$ pulses. In fact, each $^LP$ pulse serves as a gate or switch control signal to multiplexer 24, and the digital data appearing at A/D converter 22 during an $^LP$ pulse is entered into the 1st stage of the memory 23 at the negative transition of MC occurring near the end of the $^LP$ signal (If the time-overlap of the clock transition and the $^LP$ pulse is insufficient to allow entry of the data, it may be necessary to adjust the relative timing, as by shifting or slightly extending the period of one-shot 34). The first four $^RP$ pulses are timed to load into latch 25 the word appearing in the Mth stage of the shift register immediately prior to clock cycles 1,002,001; 1,003,002; 1,004,003; and 1,005,004 respectively. Similarly, the fifth $^RP$ pulse is timed to load latch 25 with the word appearing in the Mth stage immediately prior to the next, or 1,005,005th, clock cycle, thereby decrementing or shortening the data storage delay time for that word by 1,000 clock cycles.

The retiming pulse, $^EP$, is generated by applying the master clock MC to the input of $(M+1)$ $(n)$ counter 70 and extending the output thereof through OR gate 72 to the input of one-shot 74. One-shot 74 has a period of ½ MC and generates an $^EP$ pulse of that duration when the output of counter 70 makes a negative transition. Similarly, the output of one-shot 60 is extended through OR gate 72 to the input of one-shot 74 to generate an $^EP$ pulse when one-shot 60 makes its negative transition. The $^EP$ pulse is extended to an input of, and through, AND gate 76 to the output thereof when the RETRACE signal extended to the other input of AND gate 76 is in the logic "1" state.

Counter 70 provides an output transition (and thus an $^EP$ pulse) following each count of $(M+1)$ $(n/n+1)$ clock pulses MC. If the product of $(M+1)$ and $(n/n+1)$ is a non-integer, the next higher integer is chosen to facilitate generation of the pulses with standard counter circuits and to insure that the $^EP$ pulse for retiming the data word associated with the nth $^RP$ pulse does not precede the data byte. In the illustrated embodiment, counter 70 provides an output transition at intervals of 801 clock pulses MC. In order to insure that an $^EP$ pulse occurs after the nth $^RP$ pulse but before the $n+1$th $^RP$ pulse occurring $^TMC$ later, the output of $(n)$ counter 58, delayed by ½ MC through one-shot 60, is applied to one-shot 74 through OR gate 72, as mentioned above.

The $^EP$ pulses are extended through an OR gate 78 to the reset input of counter 70 to reset the counter during each $^EP$ pulse. The RETRACE signal is applied to another input of OR gate 78 inhibit operation of counter 70 throughout the retrace phase of each sweep cycle.

Referring to FIG. 5, it will be seen that each $^EP$ pulse occurs intermediate an adjacent pair of $^RP$ pulses for the purpose of relocking the data word associated with the earlier of the two $^RP$ pulses in the pair. No $^EP$ pulse occurs to retime and readout the word stored in latch 25 by the "final" $^RP$ pulse in the trace phase of the sweep cycle, however loss of this word is inconsequential inasmuch as substantially all of the foregoing data has been retained.

It should be understood that if some degree of distortion in the resulting analog waveform 11 is acceptable, it would be possible to omit each $n+1$th $^RP$ pulse (and similarly, the respective $^EP$ pulse) in the recursive sequence of $^RP$ pulses discussed. Instead, each recursive sequence of $^RP$ pulses would be comprised of $n$ pulses (4 instead of 5), with the interval between $n-1$ successive pulses corresponding with that of the "longer" interval between $n$ of the earlier described $^RP$ pulses and the interval between the $n-1$th and nth pulses being longer by $^TMC$ than the so-called "longer" interval. This sequence of $^RP$ pulses will effect the necessary decrementation of the total storage length of memory 23 in essentially the same manner as previously described, however, each $n+1$th word will now be lost. An example of this is shown in the $^RP$ pulse train of FIG. 5 in which the pulse normally occurring at clock cycle 5,000,995 is dotted to illustrate the possibility of its omission. However, assuming 80-100 samples are taken to represent each PQRST complex of an ECG waveform, loss of each $n+1$th sample (where $n$ may be 5-10) should not seriously distort the compressed analog waveform 11, particularly in view of the filtering action of D/A converter 27.

The invention would also find utility in those data processing systems in which continuously available input data is to be output in its entirety on a channel during a first phase or portion of each operation cycle, and additional other data (possibly derived from the data in the first phase of the cycle) is to be output on the same channel during the second phase of the cycle.

While a preferred embodiment of the invention has been shown and described, various modifications and substitutions may be made thereto without departing from the spirit and scope of the present invention. Accordingly, it is to be understood that the present invention has been described by way of illustration and not limitation.

We claim:

1. A system for the cyclical time-compression of a signal waveform comprising:

a recirculating memory of predetermined time-quantized length, said memory providing a storage delay corresponding with the product of said predetermined time-quantized length and the number of passes through said memory;

means having successive samples of the signal waveform extended thereto and being responsive to first timing signals for entering respective said samples of the signal waveform into said memory;

means for generating and applying a plurality of said first timing signals to said data entry control means throughout a time-compression cycle, said first timing signals recurring at an interval corresponding with the interval between successive samples of the signal waveform, said first timing signals having an interval such as to cause precession of the samples in the memory, and a predetermined number of the samples being entered in said memory during a first fraction of each time-compression cycle;

means responsive to second timing signals for selectively interrogating said memory and providing read out of the respective interrogated samples; and means for generating and applying said second timing signals to said memory interrogation means following a time delay, comprising said first fraction of each time-compression cycle, the remaining fraction of each said time-compression cycle being a compressed-time cycle in which the timing of said second timing signals is such that the storage delay of said recirculating memory is decremented from a maximum to a minimum over said compressed-time cycle whereby said interrogated samples cumulatively substantially represent the signal waveform in time-compression.

2. The time-compression system of claim 1 wherein said data entry control means and said memory interrogation means respectively have fixed access to said recirculating memory, and said second timing signals occur successively in said compressed-time cycle following first and second intervals of different length thereby to effect said decrementation of the apparent time-quantized length of said recirculating memory.

3. The time-compression system of claim 2 wherein the time-quantized length of said recirculating memory comprises a predetermined number of serially connected stages of storage clocked at a predetermined shift rate, said first interval between successive said second timing signals corresponds with that of said first timing signals thereby to maintain a particular apparent time-quantized length of said recirculating memory, and said second timing signals occurring at said second interval being regressed one stage of memory storage relative to the respective immediately preceding second timing signal thereby decrementing the apparent time-quantized length of said memory.

4. The time-compression system of claim 3 wherein the number of said second timing signals occurring within said compressed-time cycle is substantially the same as the number of said first timing signals occurring within said time-compression cycle thereby to provide readout of substantially all of the samples entered into said memory during said time-compression cycle.

5. The time-compression system of claim 4 wherein the ratio of the number of said second timing signals occurring at said second interval relative to those occurring at said first interval within a said time-compression cycle corresponds with the ratio of said first fraction to said remaining fraction of a said time-compression cycle.

6. The time compression system of claim 4 wherein said first and second intervals at which said second timing signals occur are interspersed, thereby resulting in a rhythmic pattern of said second timing signals.

7. The time-compression system of claim 6 wherein said interspersal of said first and second intervals between successivve said second timing signals comprises each "$n$" successive second timing signals occurring at said first interval being immediately followed by a single second timing signal occurring at said second interval, where "$n$" represents the ratio of the length of said remaining fraction to said first fraction of said time-compression cycle.

8. The time compression system of claim 7 wherein "$n$" is an integer.

9. The time-compression system of claim 2 wherein the time-quantized length of said recirculating memory comprises the product of a predetermined number of stages of storage and the period of the clock signal applied to said storage stages for the serial shift of samples stored therein, and the interval at which said first timing signals recur is greater than the time-quantized length of said memory by the interval commensurate with a single repetition of the storage shift clock signal whereby said samples in said memory precess one storage stage for each successive one of said first timing signals.

10. The time-compression system of claim 8 wherein the time-quantized length of said memory and the interval between successive said first timing signals are selected such that said memory is substantially exactly filled with successive samples of the signal waveform during said first fraction of said time-compression cycle.

11. The time-compression system of claim 1 including first means for converting the magnitude of said signal waveform to a digital sample, means for operating periodically said first converting means at the repetition rate of said first timing signals whereby said waveform samples are said digital samples, and second means for converting said digital samples in time-compression from said memory interrogation means to a respective time-compressed analog signal waveform.

12. The time-compression system of claim 11 wherein said memory interrogation means includes first storage means responsive to said second timing signals for selectively interrogating said memory and temporarily storing the respective interrogated digital sample, second storage means having the output of said first storage means extended thereto and responsive to third timing signals for temporarily storing the respective digital sample appearing at said first latch, and means for generating and applying said third timing signals to said second storage means during said compressed time cycle, said third timing signals recurring at substantially constant intervals and in substantially the same number as said second timing signals during said compressed-time cycle thereby to equalize the timing of said interrogated digital samples being readout.

13. The time-compression system of claim 1 wherein the signal waveform is for display by means having a plurality of two phase display cycles, said first fraction of each said time-compression cycle corresponding with one phase of each said display cycle, and each said compressed-time cycle corresponding with the other phase of each said display cycle thereby to display the signal waveform in time-compression substantially in its entirety during the said other phases of respective said display cycles.

14. In a signal waveform processing and display system,
display means responsive to a cyclical control signal for alternately displaying and interrupting the display of a particular input data signal extended thereto;
means for generating said display control signal;
means providing a continuous source data waveform signal for display by said display means;
means for periodically sampling the waveform to provide sequential waveform data samples;
memory means for storing said data samples for differing periods of time until respective readout;
means for continuously entering a plurality of said data samples sequentially into said memory at a first average rate throughout each of a succession of time-compression cycles of predetermined duration; and means responsive to said data samples and said display control signal for cyclically time-compressing said source waveform signal to cyclically present said source waveform in time compression during only the displaying phase of said display control signal as said particular input data signal to said display means, said time-compression means including means for interrogating said memory throughout only a predetermined latter portion of the duration of each time-compression cycle at a second average rate having the same ratio to said first average rate as the duration of said time-compression cycle has to the duration of said latter portion thereof to read respective said data samples out of memory in the same sequence as entered whereby data samples are read out of memory at an average rate faster than said entry rate such that said source data waveform is displayed substantially in its entirety on said display means.

* * * * *

UNITED STATES PATENT AND TRADEMARK OFFICE
CERTIFICATE OF CORRECTION

PATENT NO. : 4,109,243
DATED : August 22, 1978
INVENTOR(S) : Christopher C. Day and Robert Lee Cannon It is certified that error appears in the above-identified patent and that said Letters Patent are hereby corrected as shown below:

In column 9, lines 11 and 12 should read --a respective $E_p$ pulse. Stated another way, for (n + 1) (M) words (5 x 1000 = 5,000) stored during a full sweep--;

In column 11, line 66, delete "relocking" and insert --reclocking--;

In column 13, line 56, delete "successivve" and insert --successive--.

Signed and Sealed this

Twenty-fourth Day of April 1979

[SEAL]

Attest:

RUTH C. MASON
Attesting Officer

DONALD W. BANNER
Commissioner of Patents and Trademarks